US010502846B2

(12) United States Patent
Lage et al.

(10) Patent No.: US 10,502,846 B2
(45) Date of Patent: Dec. 10, 2019

(54) NORMALIZATION CORRECTION FOR MULTIPLE-DETECTION ENHANCED EMISSION TOMOGRAPHY

(71) Applicants: Eduardo M. Lage, Boston, MA (US); Joaquin L. Herraiz, Boston, MA (US); Vicente J. Parot, Cambridge, MA (US); Shivang R. Dave, Boston, MA (US)

(72) Inventors: Eduardo M. Lage, Boston, MA (US); Joaquin L. Herraiz, Boston, MA (US); Vicente J. Parot, Cambridge, MA (US); Shivang R. Dave, Boston, MA (US)

(73) Assignee: Massachusetts Institute of Technology, Boston, MA (US)

( * ) Notice: Subject to any disclaimer, the term of this patent is extended or adjusted under 35 U.S.C. 154(b) by 935 days.

(21) Appl. No.: 14/897,105

(22) PCT Filed: Jun. 24, 2014

(86) PCT No.: PCT/US2014/043826
§ 371 (c)(1),
(2) Date: Dec. 9, 2015

(87) PCT Pub. No.: WO2014/209972
PCT Pub. Date: Dec. 31, 2014

(65) Prior Publication Data
US 2016/0131774 A1    May 12, 2016

Related U.S. Application Data

(60) Provisional application No. 61/838,846, filed on Jun. 24, 2013.

(51) Int. Cl.
*G01T 1/29*    (2006.01)
*G01T 1/164*    (2006.01)
(Continued)

(52) U.S. Cl.
CPC ............ *G01T 1/2985* (2013.01); *A61B 6/037* (2013.01); *A61B 6/481* (2013.01); *A61B 6/5205* (2013.01);
(Continued)

(58) Field of Classification Search
CPC ....... A61B 6/481; A61B 6/5217; A61B 6/037; A61B 6/5205; A61B 6/5258; A61B 6/4258; A61B 6/508; G01T 1/2985; G01T 1/1647
See application file for complete search history.

(56) References Cited

U.S. PATENT DOCUMENTS 3,786,256 A * 1/1974 Untermyer ............. G01N 23/09
250/363.01
4,071,761 A * 1/1978 Horrocks .................. G01T 1/20
250/369

(Continued)

OTHER PUBLICATIONS

International Search Report under dated Nov. 3, 2014 in connection with PCT/US2014/043826.

*Primary Examiner* — Bo Joseph Peng
(74) *Attorney, Agent, or Firm* — Quarles & Brady LLP

(57) ABSTRACT

A method and system for acquiring a series of medical images includes acquiring imaging data, identifying double coincidence events and multiple detection (MD) coincidence events from the imaging data, and storing the double coincidence events and the MD coincidence events in a first dataset and a second dataset, respectively. The method also includes applying a normalization correction to the first dataset and/or the second dataset using normalization values based on double coincidence events and/or MD coincidence events to obtain at least one normalized dataset, and reconstructing a series of medical images of the subject from the at least one normalized dataset.

7 Claims, 7 Drawing Sheets

(51) Int. Cl.
*A61B 6/03* (2006.01)
*A61B 6/00* (2006.01)

(52) U.S. Cl.
CPC .......... *A61B 6/5217* (2013.01); *A61B 6/5258* (2013.01); *G01T 1/1647* (2013.01); *A61B 6/4258* (2013.01); *A61B 6/508* (2013.01)

(56) References Cited

U.S. PATENT DOCUMENTS

| | | | |
|---|---|---|---|
| 2008/0111081 A1* | 5/2008 | Chuang | G01T 1/1603 250/363.03 |
| 2010/0219346 A1 | 9/2010 | Daghighian | |
| 2011/0073764 A1* | 3/2011 | Woldemichael | G01T 1/1647 250/362 |
| 2012/0087697 A1 | 4/2012 | Xie et al. | |
| 2012/0290519 A1* | 11/2012 | Fontaine | G01T 1/2985 706/20 |

* cited by examiner

NORMALIZATION CORRECTION FOR MULTIPLE-DETECTION ENHANCED EMISSION TOMOGRAPHY

CROSS-REFERENCE TO RELATED APPLICATIONS

This application represents the national stage entry of PCT International Application No. PCT/US2014/043826 filed Jun. 24, 2014, which claims priority to U.S. Provisional Application Ser. No. 61/838,846, filed Jun. 24, 2013, the disclosures of which are incorporated by reference here in their entirety for all purposes.

STATEMENT REGARDING FEDERALLY SPONSORED RESEARCH

N/A

BACKGROUND OF THE INVENTION

The present invention relates to systems and methods for emission tomography and, more particularly, to systems and methods for multiple-detection (MD) enhanced emission tomography that provides an increase in the performance of current emission tomography scanners by allowing the counting and effective use for image reconstruction of coincidences involving three or more photons. Such coincidences include, but are not limited to, coincidences caused by inter-detector scattered photons, random coincidences involving more than two photons, and multiple-photon events caused by radionuclides that emit prompt gamma rays in coincidence with positron emission.

There are a variety of emission tomography imaging systems and methods. One clinically important example is positron emission tomography (PET) which, generally, utilizes an administered radionuclide to acquire two-dimensional and three-dimensional tomographic images of a target area or organ of interest in a subject. More specifically, such radionuclides are employed as radioactive tracers called "radiopharmaceuticals" by incorporating them into substances, such as glucose or carbon dioxide, or molecules specifically designed to bind a predetermined target (for example, an antibody targeting a cell surface protein). These radiopharmaceuticals are then administered to the patient where they become involved in biological processes such as blood flow; fatty acid and glucose metabolism; and protein synthesis. Through a respective biological process, the radiopharmaceuticals accumulate in, or otherwise target, the area or organ of interest in the subject. By measuring or identifying photons emitted from the area or organ of interest by the accumulated or targeted radiopharmaceutical, clinically useful biological and physiological information can be acquired from the area or organ of interest.

For example, in PET, as the injected radioactive tracer decays, it emits positrons. The positrons travel a very short distance before they encounter an electron and, when this occurs, the positrons are annihilated and converted into two high-energy photons, or gamma rays. This annihilation event is characterized by two features that are pertinent to PET imaging. Namely, each gamma ray has an energy of 511 keV and the two gamma rays are directed in substantially opposite directions. An image is created by determining the number of such annihilation events at each location within the scanner's field of view (FOV).

To create such an image, typical PET scanners consist of one or more rings of detectors which are positioned to encircle the patient. Coincidence detection circuits connected to the detectors record only those photons that are detected simultaneously by two detectors located on opposite sides of the patient and that fall within an energy acceptance window around 511 keV. The number of such simultaneous events indicates the number of positron annihilations that occurred along a line joining the two opposing detectors. Within a few minutes, millions of events can be recorded to indicate the number of annihilations along lines joining pairs of detectors in the ring. These numbers are employed to reconstruct an image using well-known tomographic reconstruction techniques.

For example, current clinical (and most preclinical) PET scanners and systems usually consist of a ring 100 of block detectors 102 for detecting emitted photons, typically in circular, such as the array shown in FIG. 1, or in hexagonal or octagonal arrays. Block detectors 102 typically include a piece of scintillator material that converts the energy deposited by gamma rays into visible light. The scintillator material is usually segmented into many scintillation crystal elements configured in an array, which is read out by a number of individual photo-detectors (typically, photo-multiplier tubes (PMTs), a position-sensitive photo-multiplier tube (PS-PMT), or silicon photo-multipliers (Si-PM)) that convert the light emitted by the scintillation material into electrical signals whose magnitude is proportional to the energy deposited by the gamma rays in the scintillator material. By combining the output signals of the photon detector(s) of the block detector, it is possible to determine the single crystal in which the detected photon interacted and the energy deposited by such photon.

Although block detectors have been demonstrated as the most cost-effective solution for the implementation of PET scanners, these detectors also present some drawbacks. One drawback is that, since each detector element is a block, if several photons interact simultaneously on the same block and the added energy of those photons is within a predefined energy acceptance window (around 511 keV), it is not possible to determine from the output signals of the detector if they were produced by the interaction of a single photon (thereby presenting useful information) or by the interaction of multiple photons (thereby presenting distorted or non-useful information).

In addition, as shown in FIG. 1, the ring of block detectors 100 of a PET scanner includes individual detectors that are operated in coincidence with a fan beam 104 of block detectors on the opposite side of the ring 100. The inner circle 106 formed by edges of all such fan beams defines the useful field of view. Data is usually recorded simultaneously for all possible fan beams, and the PET scanner will produce an output whenever two photons are detected in opposite block detectors of a fan beam 104 within a specified coincidence timing window (for example, in the range of hundreds of picoseconds to tens of nanoseconds) and when both events fall into a predetermined energy window (usually from 511 keV$-\Delta E_1$ to 511 keV$+\Delta E_2$ where $\Delta E_1$ and $\Delta E_2$ are chosen as function of the energy resolution of the block detectors). Any such events are called prompt coincidences, but can be of three specific types: true coincidences, scatter coincidences, and random coincidences. In some cases, prompt coincidences (that is, any coincidence involving two photons) may be simply referred to as coincidences, in comparison to multiple-detection (MD) coincidences or multiple interaction photon (MIP) coincidences, which include coincidence events involving three or more detected photons, as further described below.

True coincidences occur when two photons 200 and 202 produced from the same positron annihilation 204 are detected within the time and energy windows of the system, as shown in FIG. 2A. Scatter coincidences occur when at least one of the photons undergoes scattering in the object under study, for example, where the photon loses a fraction of its total energy in the scatter interaction with the object before its detection. The scatter coincidence is thus detected in a pair of detectors that are non-collinear with the originating annihilation, as shown in FIG. 2B. Random coincidences, also known as accidental coincidences, occur when annihilation photons 200a and 202b from two unrelated positron annihilation events 204a and 204b are detected in opposite detectors, as shown in FIG. 2C. True coincidences produce valid information, while both scatter coincidences and random coincidences produce distorted information. In particular, scatter and random coincidences yield incorrect positional information, as shown by the dotted lines in FIGS. 2B and 2C, and contribute to a relatively uniform background noise in the resulting image, which results in a loss of contrast.

With respect to scatter coincidences, such events are typically assumed to occur only due to scattering within the patient, as shown in FIG. 2B, and current PET systems include scatter correction procedures based on this assumption. However, there are a large number of events in which Compton scattering occurs in the block detectors of the scanner, as shown in FIGS. 3A and 3B, depositing a fraction of the total energy of the photon in each interaction. In particular, FIG. 3A illustrates a scatter event where one of the photons from an annihilation event (photon A) interacts by photoelectric effect depositing energy in a detector within the acceptance energy window of the scanner, and the other photon (photon B) interacts by Compton scatter in another detector, where it deposits some of its energy, with the scattered photon (photon C) escaping from the detector ring. Consequently, the scanner will process such an event as a prompt coincidence and will accept or discard the event depending on the energy of photon B. More specifically, if the energy of photon B is within the scanner's energy acceptance window, it will be labeled as a true coincidence event and accepted. If the energy of photon B is not within the energy acceptance window, it will be labeled as a scatter coincidence event and discarded.

FIG. 3B illustrates an inter-detector scatter (IDS) event, which is a specific case of an MD event (that is, an event involving more than two detected photons). The IDS event of FIG. 3B occurs when one of the photons from an annihilation event (photon A) interacts by photoelectric effect depositing energy in a detector within the acceptance energy window of the scanner (that is, 511 keV$-\Delta E_1$ to 511 keV$+\Delta E_2$), and the other photon (photon B) interacts by Compton scattering in another detector. Photon B deposits some of its energy in the detector it is incident upon, and the scattered photon (photon C) produced by the Compton scattering event deposits energy in another detector. Consequently, multiple photons (three, in this example) are detected within the time window of the scanner and this MD event could be processed to obtain useful information.

With respect to random coincidences, events (that is, random MD events) can involve more than two photons from at least two different decays within accepted energy and timing windows. When random MD events are detected, current PET scanners either reject the multiple detected photons or erroneously select one or more photon pairs and respective lines of response (for example, as a function of the timing and/or energy of the detected photons). When the photons from the MD event originate from the same annihilation process, the MD event can be processed to obtain useful information. For example, FIG. 3C illustrates a random MD event where three photons, photon A, photon B, and photon C, are detected within the coincidence and energy windows of the scanner. In this example, photons A and B come from the same annihilation event, whereas photon C originates from a different annihilation event. As photons A and B arise from the same positron-electron annihilation, the line A-B contains useful information while lines A-C and B-C do not. Alternatively, some detected random MD events originate from N different annihilations (where N is the number of photons involved in the MD event). While such an event has a lower probably of occurring, the processed event would not provide any useful information. For example, FIG. 3D illustrates a random MD interaction in which three photons, photon A, photon B, and photon C, are generated by three different annihilations. In this example, none of the possible lines of response (that is, line A-B, line A-C, or line C-B) provide useful information.

In addition, there are several radionuclides of interest to emission tomography that emit prompt gamma rays in coincidence with the emission of a positron. More specifically, a radionuclide decays by positron emission and, after a short delay (in the range of picoseconds), one or more prompt gamma rays are also emitted. This results in MD events (considered positron-gamma MD events) involving simultaneous detection of more than two gamma rays coming from the same nuclear decay. Examples of such radionuclides that are capable of causing such events (considered positron-gamma emitters) include, but are not limited to, iodine-124 ($^{124}$I), bromine-76 ($^{76}$Br), yttrium-86 ($^{86}$Y), rubidium-82 ($^{82}$Rb), and technetium-94m ($^{94m}$Tc). FIG. 3E illustrates an example positron-gamma MD event that may occur when using a positron-gamma emitter with a state-of-the-art PET scanner. In this example, photon A, photon B, and prompt gamma ray C are generated from an annihilation. If the energy of prompt gamma ray C is within the energy acceptance window of the scanner, the event may be processed similar to the random MD events described above with respect to FIGS. 3C and 3D, where a line of response is selected as a function of the timing resolution and/or energy resolution of the scanner. If the energy of prompt gamma ray C is over or under the energy acceptance window of the scanner, the scanner may treat the event as a true coincidence and select the appropriate line of response (that is, line A-B) using suitable criteria.

In current clinical and preclinical PET scanners, no viable information is obtained when the above-described MD events occur (that is, the IDS event of FIG. 3B, the random MD events of FIGS. 3C and 3D, and/or the positron-gamma MD event of FIG. 3E) because multiple detections are not identified as valid events by the scanner's coincidence system and, thus, are rejected or erroneously included as double-coincidence events. Although, in some cases, the IDS event shown in FIG. 3A may be detected and processed in the same fashion as scatter events that have undergone scattering in the object, such as that shown in FIG. 2B. In other words, data collected for events comprising more than two detections is usually thrown out and only data from prompt coincidences (including true coincidences, in-body scatter coincidences, random coincidences, crystal scatter coincidences with two detection events, and in general any type of two-photon coincidence events within time and energy acceptance windows) are used to compose images, thus limiting the potential sensitivity of the system and quality of the resulting images.

Therefore, it would be desirable to have a system and method for emission tomography imaging that controls for data collected from MD events and, additionally, may effectively use these events for generating improved images without introducing artifacts.

SUMMARY OF THE INVENTION

The present invention overcomes the aforementioned drawbacks by providing a system and method for emission tomography that enables the use of data from multiple-detection (MD) events (that is, events in which three or more photons are detected in coincidence) during data processing and image reconstruction. The present invention further provides a normalization correction and reconstruction process to effectively use such data for improving image quality. Thus, the present invention provides an improvement in scanner performance, due to the use of both traditional prompt coincidence data, as well as MD coincidence data. This configuration can be adopted in existing preclinical and clinical imaging systems, such as PET scanners, without requiring additional or other non-conventional detector elements.

In accordance with one aspect of the present invention, a method for acquiring a series of medical images of a subject using an emission tomography system is provided. The method includes acquiring imaging data, identifying double coincidence events from the imaging data, and storing the double coincidence events in a first dataset. The method also includes identifying MD coincidence events from the imaging data and storing the recovered MD coincidence events in a second dataset. The method further includes applying a normalization correction to the first dataset and/or the second dataset using normalization values based on double coincidence events and/or MD coincidence events to obtain at least one normalized dataset, and reconstructing a series of medical images of the subject using the at least one normalized dataset.

In accordance with another aspect of the present invention, an emission tomography system is disclosed for acquiring a series of medical images of a subject. The system includes a plurality of radiation detectors configured to be arranged around the subject to acquire photons emitted from the subject as a result of a radionuclide administered to the subject and communicate signals corresponding to acquired photons. The system also includes a data processing system configured to receive the signals from the plurality of detectors, determine, from at least the signals from the plurality of detectors, coincidence events including photon coincidence events involving two photons and photon coincidence events involving at least three photons, map the photon coincidence events involving two photons to projected lines of response, and map the photon coincidence events involving at least three photons to the projected lines of response. The data processing system is also configured to apply a first normalization correction to the mapped coincidence events involving two photons based on a first normalization using two-photon events and apply a second normalization correction to the sorted photon coincidence events involving at least three photons based on a second normalization using coincidence events involving at least three photons. The system further includes a reconstruction system configured to receive an array of normalized photon coincidence events involving two photons and normalized photon coincidence events involving at least three photons from the data processing system and reconstruct therefrom a series of medical images of the subject.

In accordance with yet another aspect of the present invention, a method for acquiring a series of medical images of a subject is disclosed. The method includes detecting photons emitted from the subject in response to a radioisotope having been administered to the subject, creating imaging data based on the detected photons, and processing the imaging data to identify timing information and energy information associated with the detected photons. The method also includes assigning the imaging data corresponding to photon coincidence events involving two photons and photon coincidence events involving at least three photons into datasets based on the timing information and the energy information, mapping the photon coincidence events involving two photons, applying a first normalization to the photon coincidence events involving two photons, mapping the photon coincidence events involving at least three photons, and applying a second normalization to the photon coincidence events involving at least three photons. The method further includes reconstructing a series of medical images of the subject from the photon coincidence events involving two photons and the photon coincidence events involving at least three photons.

In accordance with yet another aspect of the present invention, a method for acquiring a series of medical images of a subject is disclosed. The method includes detecting photons emitted from the subject in response to a radioisotope having been administered to the subject, creating imaging data based on the detected photons, and processing the imaging data to identify timing information and energy information associated with the detected photons. The method also includes assigning the imaging data corresponding to photon coincidence events involving two photons and photon coincidence events involving at least three photons into datasets based on the timing information and the energy information, mapping the photon coincidence events involving two photons, mapping the photon coincidence events involving at least three photons, and reconstructing a series of medical images of the subject from the photon coincidence events involving two photons and the photon coincidence events involving at least three photons. Reconstruction includes applying a first normalization to the photon coincidence events involving two photons and applying a second, different normalization to the photon coincidence events involving at least three photons.

In accordance with yet another aspect of the present invention, a method for acquiring a series of medical images of a subject having been administered a radionuclide using an emission tomography system is disclosed. The method includes acquiring imaging data from the subject that includes triple coincidence events, analyzing the imaging data to identify triple coincidence events from the imaging data; and analyzing the triple coincidence events to differentiate between inter-detector scatter (IDS) events, random triple events, and positron-gamma events. The method also includes segregating the triple coincidence events based on the differentiations between the IDS events, the random triple events and the positron-gamma events and reconstructing an image of the subject using the imaging data.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 2A:
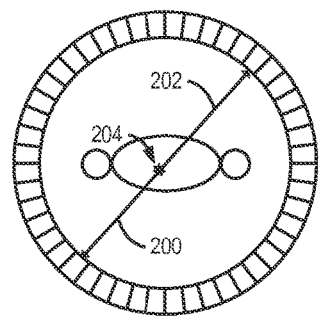
FIGS. 2A-2C are schematic views of prompt double coincidence events in a PET system, including a true coincidence event (FIG. 2A), a scatter coincidence event (FIG. 2B), and a random coincidence event (FIG. 2C).
Figure 1:
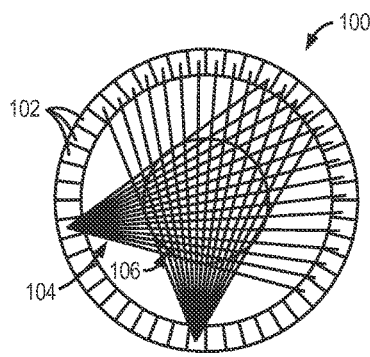
FIG. 1 is a schematic view of a ring of block detectors in a positron emission tomography (PET) system.

One of the greatest strengths of emission tomography, such as positron emission tomography (PET), is its sensitivity to true events (that is, events that provide correct information to generate an image). The sensitivity of a PET scanner is determined primarily by the absorption efficiency of the detector system and its solid angle coverage of the imaged object. Increasing the sensitivity of a PET scanner can permit, among other things, a reduction in scan time or an equivalent reduction in the amount of radioactive compound used to obtain similar quality images. The use of multiple detection (MD) coincidence events (such as inter-detector scattered (IDS) events, random MD events, positron-gamma MD events, among others) can greatly increase the sensitivity of and widen the range of applications of current clinical and preclinical PET scanners when an appropriate methodology is used to recover those events accordingly. The present invention recognizes that, independent of the recovery method, a specific correction for normalization of these events is required in order to effectively use MD events to generate images. The present invention provides a method for performing this correction for any recovery method and a processing scheme to apply the correction to data.

With respect to MD events, such as IDS events where three or more detections are present, approaches have been proposed to detect and recover such events and convert them into useful information based on a number of different recovering methods. More specifically, the objective of these methods is to determine, for each IDS event, the appropriate line of response (LOR), such as, for example, line A-B or line A-C illustrated in FIG. 3B (line B-C would not be considered a valid line because it is outside of the field of view of the scanner). Since state-of-the-art timing resolution and energy resolution of the conventional detectors employed in clinical PET systems is not enough to determine the order of detection of inter-detector scattered photons (that is, B or C of FIG. 3B), different approaches to face this problem have been proposed. These approaches are commonly based on the information provided by the scanner (including position of interaction, time of interaction, and/or energy deposited by each photon) and underlying physical properties of Compton scattering in order to assign or associate MD events to appropriate lines of response.

Also, based on the energy and timing information of each of the photons received, it is possible to determine that A-B-C interactions are due to an IDS event (as opposed to another type of MD event). For example, as described below, an IDS event can be identified when the three interactions are in coincidence, and the energy of one of the photons and the added energy of the other two photons are within the energy window of the scanner.

Some example approaches for recovering MD events include an averaging method (that is, averaging over valid LORs defined by the three interaction points, such as assigning 0.5 to LOR A-B and 0.5 to LOR A-C), a maximum/minimum energy method (that is, selecting the photon (B or C) with higher/lower energy as an endpoint for the LOR), a random method (that is, selecting photons B or C with the closer time stamp to photon A, which is considered a substantially random selection because the timing resolution of current PET scanners is not good enough to determine true chronological order), a proportional method (that is, assigning a probability to LOR A-B and LOR A-C based on the distribution of double coincidences along LOR A-B and LOR A-C), Compton kinematics, Klein-Nishina differential cross section-based algorithms, and algorithms based on combinations of the above approaches. Generally, the above approaches, or any other approach that serves to determine appropriate LOR(s) for detected MD events based on properties (such as geometric information) of single detections, may be considered recovering methods, sorting methods, processing methods, and/or mapping methods. Sorting methods may specifically refer to IDS events because the purpose of such methods is to "sort" the IDS events over time in order to determine the first detected event (that is, photon B in FIG. 3B rather than photon C) which, in turn, provides the correct LOR (that is, LOR A-B in FIG. 3B rather than LOR A-C).

In standard PET imaging (that is, only using prompt or double coincidences, sometimes simply referred to as coincidences), correction for variations in efficiency in each LOR and compensation for the geometry-dependent sensitivity variation of the scanner is known as normalization correction. Inaccurate correction of these factors can lead to rings, streaks, or other non-uniformity artifacts, thus reducing the quality and quantitative accuracy of reconstructed images. Although there are several ways of calculating and applying this correction, the most straightforward approach for normalization is to record the number of counts detected by each pair of detection elements while exposing all pairs to the same amount of radiation (such as the same radiation source that illuminates uniformly). In an ideal scanner, each detector pair should record the same number of counts (within statistical limits), but in practice some pairs record more counts than others, mainly because of efficiency variations and geometrical factors.

The acquisition time can either be a long acquisition or a shorter acquisition (for example, standard acquisition time) that includes the application of an approach to reduce statistical uncertainty. After the respective acquisition is completed (either for the longer acquisition time or the shorter acquisition time), the normalization factor for each specific LOR is generally computed as the number of occurrences of that LOR divided by the average/median/mode value of occurrences for all of the LORs in the scanner. This correction is usually applied to the projection data (usually a sinogram or LOR histogram) prior to image reconstruction when an analytic reconstruction algorithm (such as Filtered back projection, FBP) is used or may also be applied during the image reconstruction when an iterative reconstruction algorithm (such as ordered subsets expectation maximization algorithm, OSEM) is used.

Figure 4:
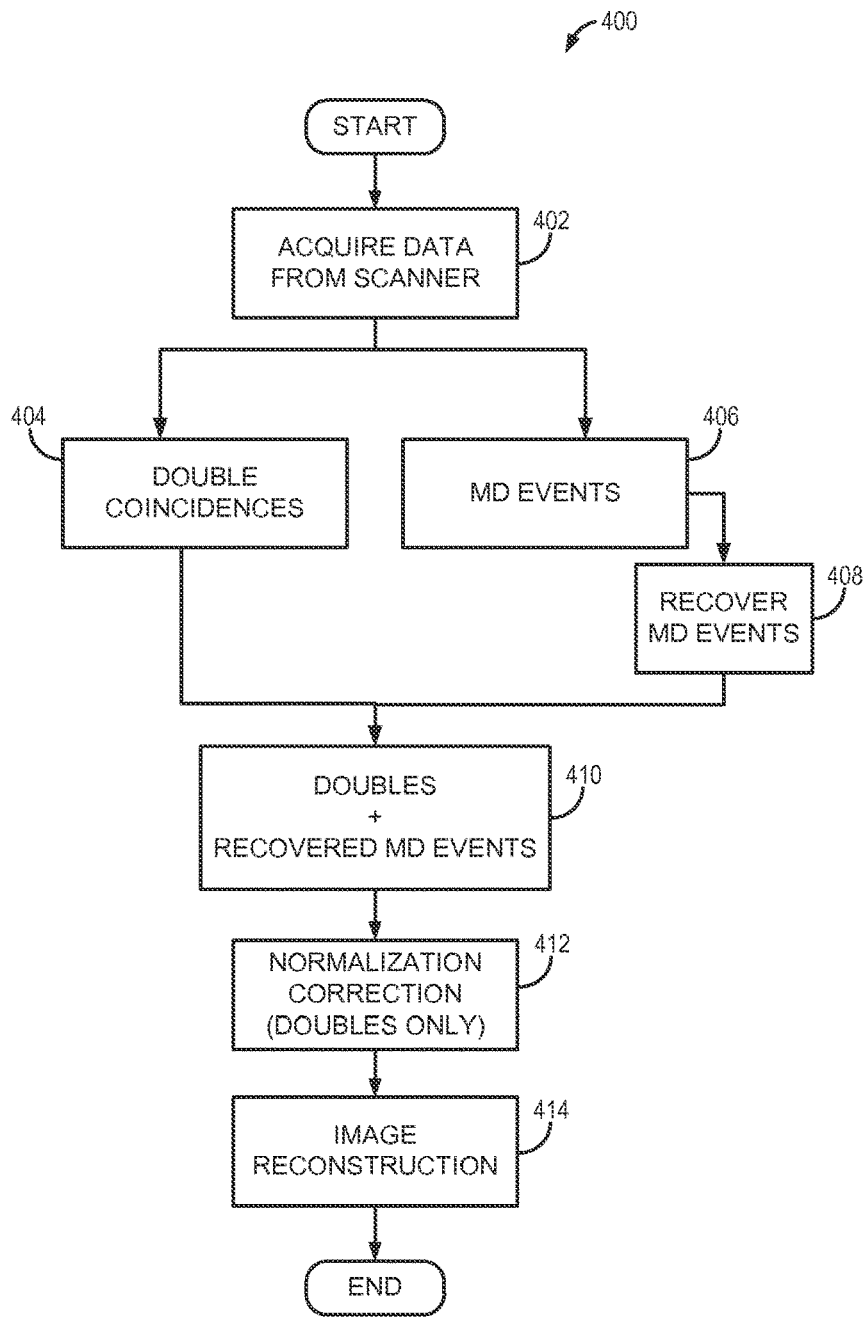
FIG. 4 is a flow chart setting forth the steps of a method for utilizing MD events in PET.

With regard to previous attempts to use certain MD events for image reconstruction, no special considerations were made for the normalization of datasets containing such events. For example, in proposed approaches for using IDS events, datasets were created containing both standard coincidences (that is, double coincidences) and recovered IDS events, and a standard normalization correction was applied solely based on information from double coincidences (as described above). This is generally illustrated in FIG. 4, that is, a process 400 where image reconstruction is completed using an analytical reconstruction algorithm and normalization is applied in a single step prior to reconstruction. As shown in FIG. 4, raw scanner data is acquired at process block 402. Double coincidence event data (that is, standard events grouped, for example, in LOR histograms) and MD event data are separately recorded into datasets at process blocks 404 and 406, respectively. MD event data is then recovered according to a desired recovery method and stored in the same format as the standard events (for example, in LOR histograms) at process block 408. The recovered MD events are then combined with the double coincidence events at process block 410. Normalization correction is then applied to both the MD events and the double coincidence events at process block 412 using a normalization factor determined from only double coincidence events (for example, from a previous calibration, as described above). Following normalization, the corrected data is reconstructed using, for example, an analytical reconstruction algorithm at process block 414.

Figure 5:
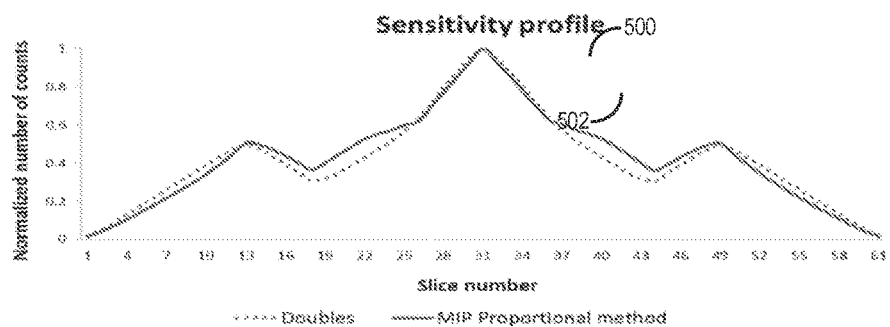
FIG. 5 is a chart comparing axial sensitivity profiles of MD coincidences and double coincidences.

Applying the above-described process 400 has been found to introduce non-uniformity artifacts in the resulting images. In other words, the calibration obtained from double coincidences is not appropriate for normalization correction of MD coincidences. For example, testing was performed by separately reconstructing only double coincidences and only recovered MD coincidence events (in this example, IDS events processed by multiple methods). The testing illustrated that, while traditional normalization correction worked sufficiently for a double coincidence dataset, it did not work properly with MD datasets. Furthermore, testing was performed to compare acquired calibration data and separately calculate normalization corrections using only double coincidences (that is, standard PET coincidences) or only MD events (in this example, IDS events processed using different methods). More specifically, in this testing, the sensitivity profiles of the datasets used to calculate each normalization correction were compared, the results of which are illustrated in FIG. 5. As shown in FIG. 5, the axial sensitivity profile 500 obtained using only MD coincidences processed by one specific method (in this case, a proportional method), illustrated by the solid line, is significantly different compared to the axial sensitivity profile 502 obtained using only standard PET coincidences, illustrated by the dotted line. Similar results were obtained using other MD recovering methods. These results indicate that the normalization obtained from double coincidences is not appropriate for normalization correction of MD coincidences obtained using any recovering method. Thus, normalization correction should match the sensitivity profile of the scanner (in the three dimensions) and, since the scanner has different sensitivity profiles for different types of coincidence events (for example, for prompt double coincidences and for IDS MD coincidences), the normalization correction for each type of coincidence event should match the sensitivity profile of the scanner for that specific type of event.

The present invention provides a method to obtain an appropriate normalization correction for MD events processed using any method and a procedure to apply that correction to the data. A normalization correction process 600 according to the present invention is illustrated in FIG. 6 and a process 700 according to the present invention for acquiring a series of medical images of a subject using an emission tomography system is illustrated in FIG. 7.

Figure 6:
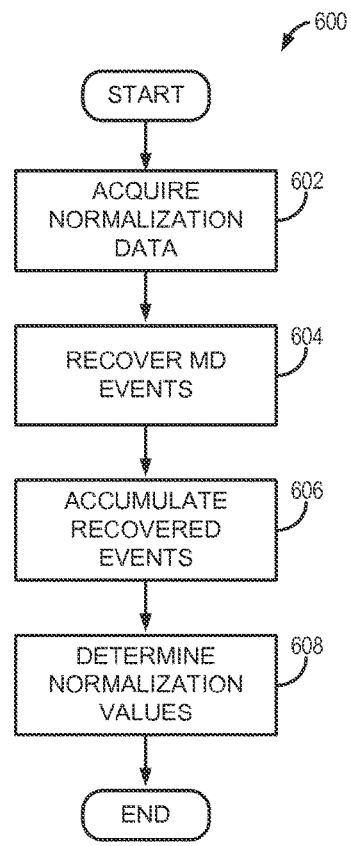
FIG. 6 is a flow chart setting forth the steps of a normalization correction method in accordance with the present invention.

As shown in FIG. 6, the normalization correction process 600 can include acquiring normalization data using one or more radiation sources exposing all detector pairs in a uniform way at process block 602. This may be the same source used to obtain normalization correction for double coincidence events. Acquisition may be completed over a sufficient time to allow a statistical significance of counts in both double and MD coincidence sets. Since sensitivity to MD coincidences in PET scanners is usually smaller than sensitivity to double coincidences, the acquisition time may be longer than the conventional time period used to obtain a correction only for double events. The MD events identified from this calibration acquisition are processed using any specific recovering method at process block 604. The specific recovering method may be dependent upon the type of MD event(s) being detected or, more specifically, upon the type of MD event(s) to be used for image generation. For example, proportional recovering methods may be used for IDS events and/or random MD events, whereas other methods may be used for positron-gamma MD events. At process block 606, the set of recovered events is accumulated in any appropriate format, such as an LOR histogram. MD normalization values for each LOR are then determined by dividing the number of MD events sorted in that LOR by the average, median, or mode number of MD events for all of the LORs in the scanner at process block 608.

This process 600 provides a second set of normalization values to be used only for MD events (that is, recovered using the same method used in process block 604), in addition to a first set of normalization values to be used only for double coincidences. Generally, if a specific recovery method is desired for use during imaging, this process 600 is executed using that specific recovery method (at process block 604) in order to provide appropriate normalization values specific to the method. Accordingly, when different types of MD events are to be utilized, this process 600 can be executed specific to the recovering method and/or the type of MD event. In addition, this process 600 may be executed separately or concurrently with a process for determining the first set of normalization values.

Figure 7:
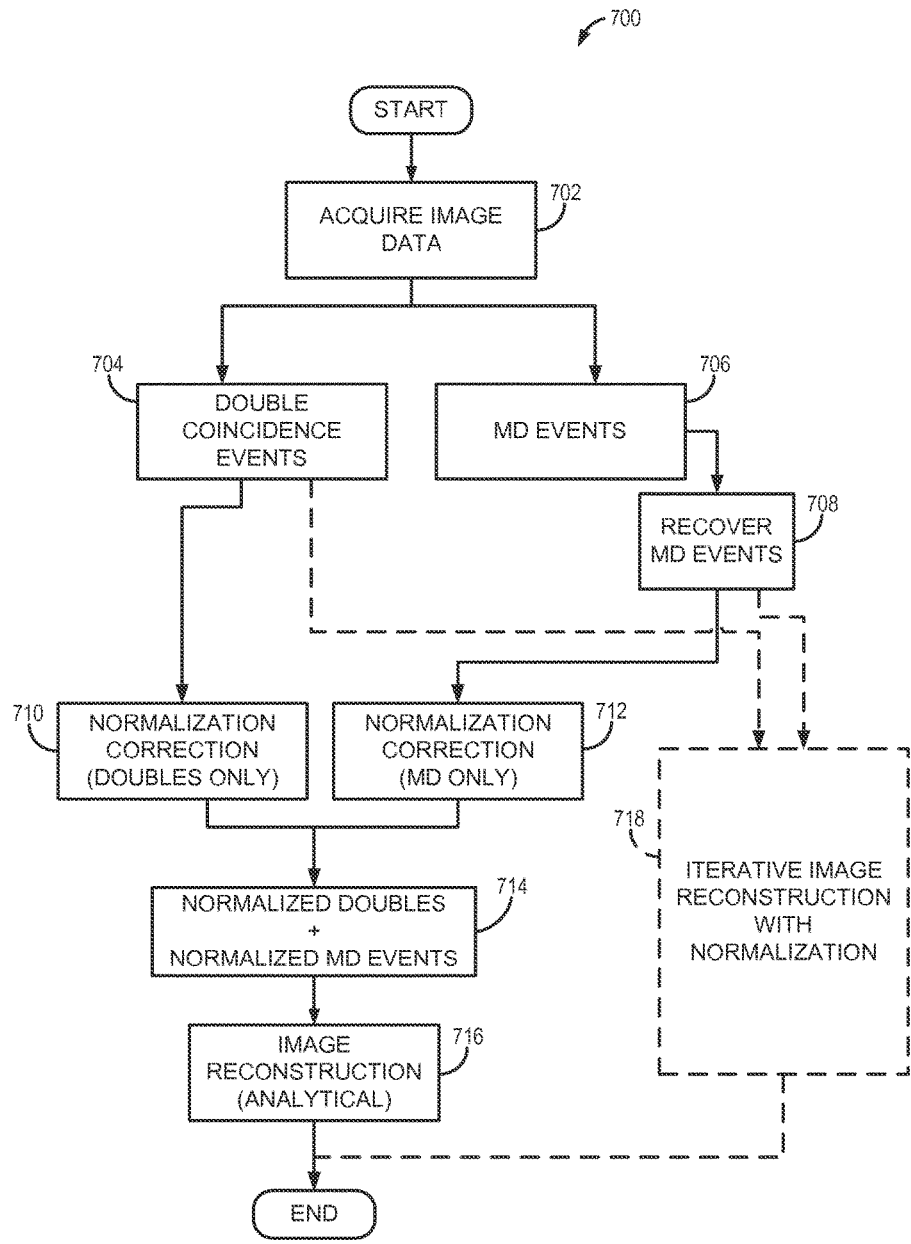
FIG. 7 is a flow chart setting forth the steps of a method for MD-enhanced emission tomography in accordance with the present invention.

With reference to FIG. 7, generally, after the normalization correction process 600 and/or after other calibration processes (such as for standard coincidences) are completed, this process 700 is completed for any subsequent PET scan. More specifically, FIG. 7 illustrates a process for MD-enhanced PET with proper normalization correction. The process 700 includes acquiring raw scanner data at process block 702, for example after a subject has been injected with a radionuclide. Following data acquisition at process block 702, double coincidence event data (that is, standard events grouped, for example, in LOR histograms) and MD event data are identified and separately recorded, or stored, into datasets at process blocks 704 and 706, respectively. As discussed above, two-photon coincidences can be considered traditional prompt coincidences, while multiple photon coincidences are indicative of MD coincidences, including IDS coincidences, random MD coincidences, positron-gamma MD coincidences, among others. At process block 708, MD event data is then processed according to a desired recovering method (that is, based on specific recovering criteria) and stored in the same or an equivalent format as the standard events (for example, in LOR histograms or sinograms). Normalization correction is then applied to the double coincidence events at process block 710 using a normalization factor determined from only double coincidence events. Normalization correction is separately applied to the recovered MD events at process block 712 using a normalization factor determined from only MD events (that is, determined through the normalization correction process 600, described above). The normalized MD events are then combined with the normalized double coincidence events at process block 714. After the normalized events are combined, the workflow of the data proceeds in a traditional manner using the combined corrected set for image reconstruction at process block 716. Thus, a set of images is reconstructed based on the double coincidence data as well as the recovered multiple photon coincidence data.

Figure 3A:
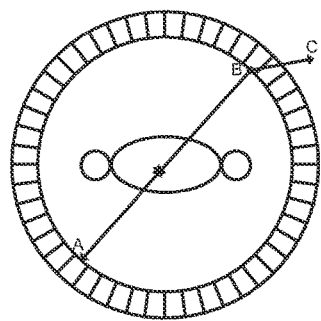
FIGS. 3A-3E are schematic views of coincidence events in a PET system, including a scatter coincidence event (FIG. 3A), an inter-detector scatter coincidence event (FIG. 3B), a random multiple detection (MD) event involving three photons (FIG. 3C), another random MD event involving three photons (FIG. 3D), and a positron-gamma MD event involving two annihilation photons and a prompt gamma ray (FIG. 3E).
Figure 3B:
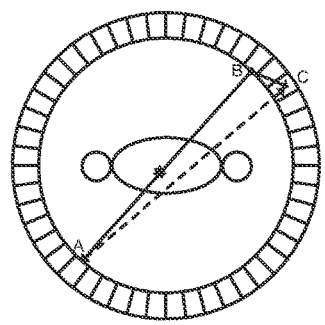

More specifically, with respect to process block 702, scanner or imaging data is acquired by detecting and recording N-photon coincidences within a coincidence window, for example on the order of picoseconds to nanoseconds, in different detectors of the scanner and across a predetermined range of energies. That is, a wide range of image data is collected to ensure that data for each type of event, including IDS events, random MD coincidence events, and/or positron-gamma MD events, is acquired. In other words, in order to detect and register certain types of MD events (that is, to accept three or more photon coincidences), a PET scanner must be configured to employ a wider energy acceptance window than the one commonly used in clinical and preclinical scanners. Since the energy window in current scanners is a narrow band centered at 511 keV, for example, events like the one shown in FIG. 3B are traditionally discarded by the software or hardware of the scanner because, although the detected photon A has an appropriate energy, generally neither photon B nor photon C is within the energy acceptance window.

At process block 704 and process block 706, two-photon coincidences and three-photon (or other multiple photon) coincidences, respectively, are identified. Two-photon (double) coincidences can be detected by a conventional set of factors, as described above, while three-photon coincidences (or other MD coincidences) can be detected by a separate set of factors. Generally, MD coincidence events can include groups of detected double coincidence events, wherein each group includes at least a first double coincidence and a second double coincidence that share a common radiation detector, or vertex (for example, in FIG. 3B, lines A-B and A-C share a common vertex at A). For sake of clarity, a three-photon coincidence, or triple coincidence, event is described herein; however, the following description can be applied to four-photon, five-photon, . . . , n-photon coincidences. The set of factors used to detect triple coincidences can include some factors similar to those required for coincident event pairs, for example wherein the time markers in each event data packet must be within a predetermined time window, such as five nanoseconds or even down to picoseconds, and the locations indicated by at least the two of the three event data packets must lie on a straight line that passes through the field of view. However, some additional factors may be required for triple coincidences that are not necessary for traditional coincidence pairs, as further described below.

First, for the case of IDS events, it is well known that for 511 keV gamma rays which interact by Compton scattering, the deviation of the resulting photon from the original trajectory or scattering angle is small (for example, between 0 and 60 degrees) with a high probability. Therefore, referring to the example inter-detector scatter event of FIG. 3B, if the residual scattered photon is also detected (photon C), it will be most likely detected in a block detector close to the one that received the first interaction (photon B). Often, this detector in a common scanner will also belong to the fan beam of detectors in coincidence with the detector that detected the interaction of photon A. Also, the sum of the energies of photons B and C must be within a range equal to 511 keV−$\Delta E_1$ to 511 keV+$\Delta E_2$ and the energy of photon A has to be within this same range to assure that this photon interacted by photoelectric effect. Observed triple coincidences that fulfill these criteria can be considered valid (or potentially useful) inter-detector scatter events.

Figure 3C:
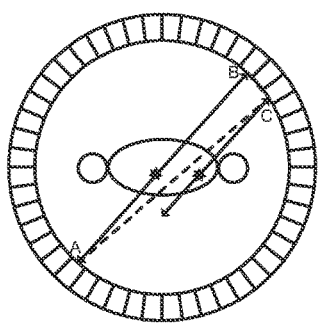
Figure 3D:
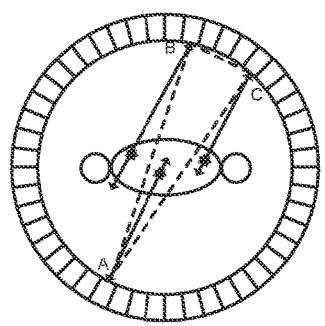

Second, for the case of random MD events, all the photons in coincidence have to deposit energy within the energy acceptance window of the scanner for double coincidences (that is, from 511 keV−$\Delta E_1$ to 511 keV+$\Delta E_2$). If a random MD event is detected based on this criteria, there is a high probability that it will be a type of detection event containing useful information, such as the example shown in FIG. 3C, rather than a non-informative type, such as the example shown in FIG. 3D.

Figure 3E:
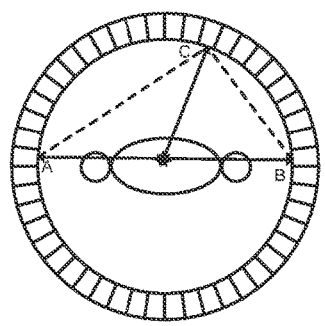

Third, for the case of positron-gamma MD events, such as the example shown in FIG. 3E, at least two photons will be within the energy acceptance window of the scanner for double coincidences (that is, from 511 keV−$\Delta E_1$ to 511 keV+$\Delta E_2$) and depending on the specific radionuclide being used, the remaining photons may be less than, within, or above the double coincidence energy acceptance window. That is, if two of the photons received (A and B) are in a given energy window and interaction C has an energy that matches the emission pattern of the radionuclide, a positron-gamma event can be determined.

Referring back to process block 704, the identified double coincidences are mapped along their respective lines of response in accordance with conventional methods. That is, coincidences are associated with specific lines of response based on the properties of the each detection, such as, for example, detector, crystal, layer, location, and the like. Using this or other information, the photon coincidence events are associated with lines of response based on the geometric information of each detection. At this point, it is possible to apply standard corrections to the double coincidence data, such as scatter or random corrections, in order to increase the signal to noise ratio (that is, true coincidences compared to the sum of in-body scattered and random coincidences).

With reference to process block 708, the MD coincidences are sorted/recovered and mapped based on any specific recovering criteria (that is, in accordance with a desired recovering method). More specifically, given the examples shown in FIG. 3B, 3C, or 3D, at this time during processing, it is still uncertain which interactions determine the true line of response containing the positron annihilation event. Thus, there are three possible lines of response along points A, B, and C, although, in these examples line B-C would not be used as a possible line of response because it does not pass through the field of view (required by the factors discussed above). State-of-the-art radiation detectors do not have sufficient timing resolution to determine the first interaction event from the time measurements, and therefore there is an uncertainty to determine if the appropriate line is A-B or A-C.

For this reason, MD coincidences are processed and stored separately from double coincidences. In order to allow the use of MD events for image reconstruction, however, it is necessary to recover the MD events into appropriate LORs. This requires distribution of the detected MD events into appropriate LORs (that is, LOR A-B or LOR A-C in the examples illustrated in FIGS. 3B, 3C, and 3E) through a sorting or recovering method. In the simplest case, an A-B-C detected MD event can be equally distributed between the subset of valid LORs. For example, if the MD event involving points A-B-C is detected N times, and the subset of valid LORs defined by points A-B-C is (A-B, A-C), N/2 counts are added to LOR A-B and N/2 counts are added to LOR A-C. In the alternative, other recovering methods, such as those described above, may be used. In the above-described case as well as with other recovering methods, whole counts or fractions of counts can be added to specific LORs. For example, using one specific recovering method, the distribution of a single MD event can result in 0.75 added to LOR A-B and 0.25 added to LOR A-C. In any event, MD coincidence counts can be distributed across the valid lines of response based on specific recovering criteria.

Once the double coincidences are mapped and the MD coincidences are recovered and mapped, it is possible to apply normalization corrections to the datasets. More specifically, normalization correction is applied to the double coincidence events at process block 710 using a normalization specific to double coincidence events. Normalization correction is separately applied to the recovered MD events at process block 712 using a normalization specific to MD events (that is, determined through the normalization correction process 600, described above, obtained using the same recovering method used in process block 708). The normalized MD event dataset is then combined with the normalized double coincidence event dataset at process block 714. After the normalized events are combined, image reconstruction is completed at process block 716.

In addition, in some applications, the double coincidence events and the MD events can be combined prior to normalization. Normalization correction is then applied to the sum of the double coincidence events and the MD events using normalization values based on a sum or weighted sum of double coincidence events and recovered MD events (that is, obtained from a normalization process, such as process 600, that uses summed double coincidence events and MD events). For example, the weighted sum can reflect the relative amount of double coincidence events and MD coincidence events. Further, in other applications, some types of MD events can be combined with the double coincidence events prior to normalization, while others can be normalized separately and combined after normalization. For example, MD events can be recovered, mapped, and/or processed separately based on their type (thus segregated into, for example, IDS events, random MD events, and positron-gamma MD events), resulting in a different MD dataset for each type of MD coincidence event. The random MD events and the positron-gamma MD events can be combined with the double coincidence events and normalized using a normalization specific to double coincidence events, while the IDS events can be normalized using a normalization specific to IDS events (or, more generally, to MD events) and then combined with the dataset containing normalized double, random MD, and positron-gamma MD events. Alternatively, each type of event (that is, double coincidence events, random MD events, positron-gamma MD events, and IDS events) can be normalized separately (based on the double coincidence normalization, a general MD coincidence normalization, or a MD coincidence normalization matched to the specific type of MD event). Thus, normalization correction for the IDS events can be different from the normalization correction for the random triple MD events and positron-gamma MD events. Also, in some applications, normalization correction for the random triple MD events and the positron-gamma MD events can be the same. The normalized events can then be combined and image reconstruction is then completed at process block 716.

At process block 716, a set of images is reconstructed, where the images are based on both double coincidence data as well as MD coincidence data. The combined corrected data can be reconstructed using an analytical reconstruction algorithm, such as FBP. The use of independently normalized MD events during image reconstruction can result in images with an increased number of counts, and consequently, increased signal to noise ratio (SNR) and increased contrast to noise ratio (CNR). More specifically, because these additional events, which are determined from data that is traditionally thrown out, can be counted and effectively used to reconstruct the images, an emission tomography system using this method 700 has a higher sensitivity in comparison to conventional PET systems and can produce better quality images in the same acquisition time or similar quality images in less acquisition time.

In some applications, process blocks 710, 712, 714, and 716 may be combined into a single image reconstruction process block 718. More specifically, in such applications, normalization corrections are applied in an iterative manner during image reconstruction, for example when iterative reconstruction algorithms (such as ordered subsets expectation maximization, OSEM) are used. The inputs to such algorithms can include the normalization correction for the double coincidences, the normalization correction for the MD coincidences, the doubles coincidence dataset, and the MD coincidence dataset(s). Accordingly, in these applications, the datasets are not normalized or combined prior to reconstruction.

The following equations represent examples in which normalization correction can be implemented in an iterative reconstruction. In equations 1, 2, and 3 below, $x^{(n)}$ denotes the activity concentration x in the n-th iteration step. The initial estimation $x^{(0)}$ can be selected as any smooth non-negative activity distribution. $g_i^D$ is the double coincidence in the LOR i, $g_i^{MD}$ is the multiple-detection coincidence in LOR and $\lambda^i$ is the estimated coincidences in i. $\alpha_{ij}$ is the probability that 2 gamma rays at voxel j are detected in LOR i. Normalization is given by $N_i^D$ for double coincidences and $N_i^{MD}$ for multiple-detection coincidences, respectively.

$$x_j^{(n+1)} = x_j^{(n)} \cdot \left[ \sum_i \alpha_{ij} \cdot \left( \frac{\frac{g_i^D + g_i^{MD}}{N_i^D}}{\lambda_i} \right) \right] \bigg/ \sum_i \alpha_{ij} \quad \text{Eq. 1}$$

Equation 1 corresponds to a reconstruction with normalization correction where both double and MD coincidences are normalized based on a double coincidence normalization factor. This equation would, for example, be applied in an iterative reconstruction with respect to the process 400 of FIG. 4.

$$x_j^{(n+1)} = x_j^{(n)} \cdot \left[ \sum_i \alpha_{ij} \cdot \left( \frac{\frac{g_i^D}{N_i^D} + \frac{g_i^{MD}}{N_i^{MD}}}{\lambda_i} \right) \right] \bigg/ \sum_i \alpha_{ij} \quad \text{Eq. 2}$$

Equation 2 corresponds to a reconstruction with normalization correction in which respective normalization is applied to the double coincidences and the MD coincidences datasets.

Also, a reconstruction with normalization correction can be used in which normalization based on a sum of double coincidence events and MD coincidence events is applied to the sum of the double coincidences and the MD coincidences datasets.

$$x_j^{(n+1)} = x_j^{(n)} \cdot \left[ \sum_i \alpha_{ij} \cdot \left( \frac{g_i^D + g_i^{MD}}{\lambda_i} \right) \right] \bigg/ \sum_i \alpha_{ij} \cdot (N_i^D + N_i^{MD}) \quad \text{Eq. 3}$$

Equation 3 corresponds to reconstruction with normalization correction in which respective normalization is not directly applied to the acquired datasets.

The above-described process 700 illustrates a basic example of the present invention; however, a number of further improvements based on state-of-the-art techniques to calculate and apply normalization correction, either using analytical or iterative reconstruction algorithms, can be used to obtain better quality images from the PET scanner.

As discussed above, several methods for recovering MD events have been proposed, and such methods have been tested using simulations. For example, for IDS events, it has been found that performance differences between these processing methods are small and that, in general, these techniques are relatively inefficient at identifying the correct LOR in the IDS event. Further results of these findings showed that utilizing IDS events results in a significant increase of apparent system sensitivity, but although the improvement can increase Signal-to-Noise ratio (SNR) in some areas of the resulting images, it does not preserve the contrast of the images reconstructed just using double coincidences and leads to a degradation of the image spatial resolution. Similar research has also been presented using real data from scanners (that is, small-animal PET systems). In this research, four different recovery algorithms were used to position the LORs coming from IDS coincidences. Reconstructed images of a standard phantom were used to measure image quality in terms of Contrast-to-Noise ratio (CNR), spatial resolution (SR), contrast recovery coefficients (CRCs), and spill-over-ratio (SOR). Although an important gain in detection efficiency was obtained from the addition of IDS coincidences, SR, CNR, SOR, and the CRCs were degraded in PET images when using IDS events and any sorting method.

Figure 8A:
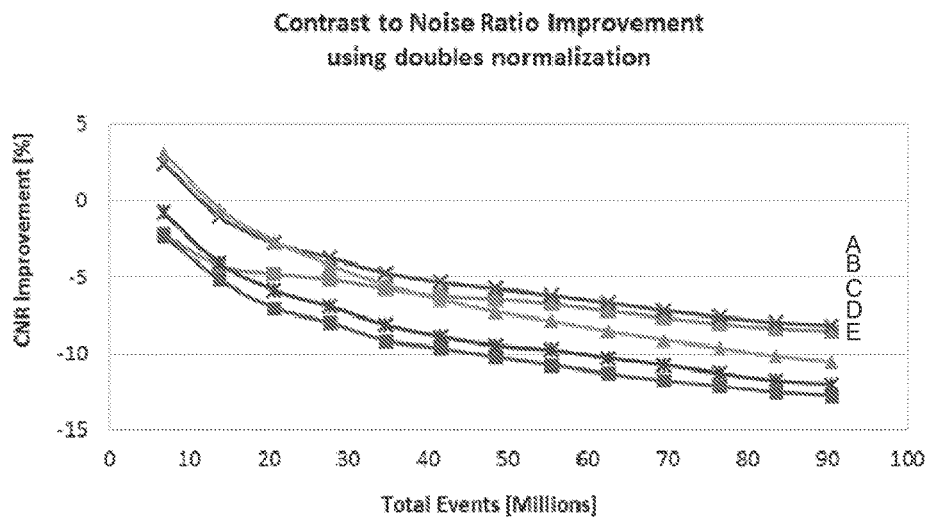
FIGS. 8A and 8B are charts comparing percent contrast-to-noise ratio (CNR) improvement of images reconstructed from datasets containing both prompt double and inter-detector scatter coincidence events (sorted by different methods) relative to that obtained from datasets containing only double coincidence events, wherein the inter-detector scatter coincidence events were normalized based on a standard normalization correction (FIG. 8A) and based on a specific MD coincidence event normalization correction in accordance with the present invention (FIG. 8B).
Figure 8B:
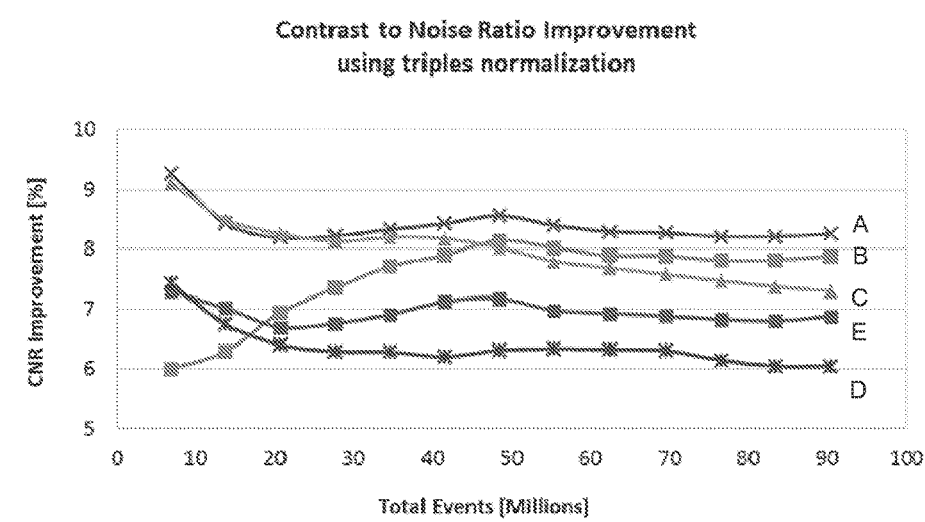

For example, FIGS. 8A and 8B illustrate percent CNR improvement of images reconstructed from datasets containing both prompt double coincidence and IDS events (sorted/recovered by different methods, A, B, C, D, and E) relative to that obtained from datasets containing only double coincidence events, plotted as a function of the number of total counts included in the image. These images were obtained from the acquisition of a standard cylindrical phantom containing an inner cylindrical compartment with an activity concentration four times that of the activity concentration of the rest of the phantom. CNR measurements were taken on a cylindrical region of interest on the images, placed in the location of the inner cylindrical compartment of the phantom. The different sorting methods applied were a proportional method (A), random method (B), maximum energy method, (C), averaging method, (D), and minimum energy method (E). Double coincidences were normalized using a standard normalization correction. FIG. 8A illustrates percent CNR improvement using IDS events, based on different sorting methods A, B, C, D, E, and applying this same standard normalization correction (that is, normalization correction obtained using only double coincidences). FIG. 8B illustrates percent CNR improvements using IDS events, based on different sorting methods A, B, C, D, E, and applying a normalization correction process according to the present invention, wherein the normalization correction was applied separately for doubles coincidence events and IDS events.

The graph of FIG. 8A illustrates that, independent of the sorting method, adding IDS events degrades image quality when standard normalization correction is applied, as evidenced by the negative CNR percentages. However, as evidenced by the positive CNR percentages illustrated in FIG. 8B, applying normalization correction using methods of the present invention results in much better performance. The improvement in CNR percentages from FIG. 8A to FIG. 8B illustrates that, independent of the recovering method, if an appropriate normalization correction is not used, adding MD events degrades image quality. On the other hand, if the above-described methods of the present invention for normalization are applied, improved image quality is obtained independent of the recovering method used.

Figure 9:
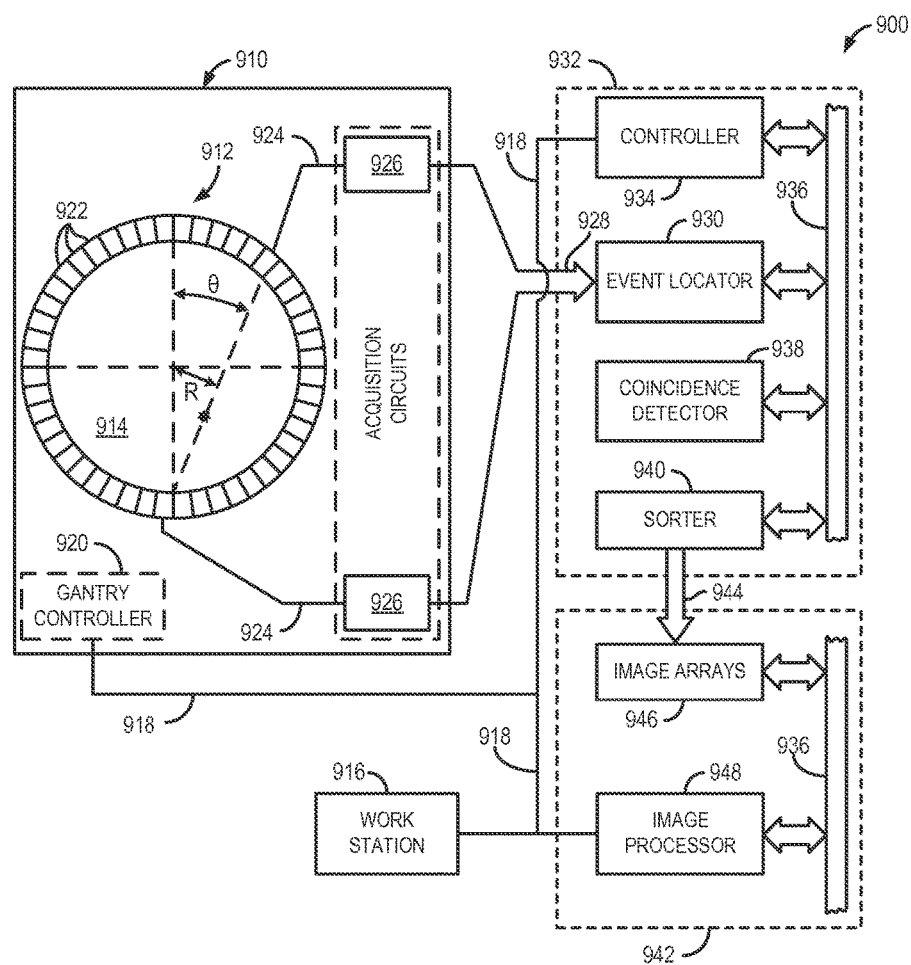
FIG. 9 is a schematic view of an emission tomography system in accordance with the present invention.

As described above, the normalization correction and imaging processes 600, 700 of the present invention may be used for improving image quality in PET systems with radiation detectors including, but not limited to, standard (that is, scintillator-type) clinical and preclinical PET systems. FIG. 9 illustrates an example PET system 900 for use with the present invention. The following paragraphs describe the components of the PET system 900 of FIG. 9 with respect to the above-described methods of the present invention.

As shown in FIG. 9, the PET system 900 includes an imaging hardware system 910 that includes a detector ring assembly 912 about a central axis, or bore 914. The bore 914 is sized to receive a subject so that the detector ring assembly 912 is arranged around the subject. An operator work station 916 communicates through a communications link 918 with a gantry controller 920 to control operation of the imaging hardware system 910.

The detector ring assembly 912 is formed of a multitude of radiation block detector units 922. Each radiation block detector unit 922 includes a set of scintillator crystals that is disposed in front of an array of photomultiplier tubes or a position-sensitive photomultiplier tube (not shown). Each photomultiplier tube produces a signal responsive to detection of a photon (such as a photon emitted from a subject as a result of a radionuclide administered to the subject) on communications line 924 when a scintillation event occurs. A set of acquisition circuits 926 receive the signals and produce signals indicating the event coordinates (x, y) and the total energy associated with the photons that caused the scintillation event. These signals are sent through a cable 928 to an event locator circuit 930. Each acquisition circuit 926 also obtains information from the detector's signals that indicates the exact moment the scintillation event took place. For example, sophisticated digital electronics can obtain this information regarding the precise instant in which the scintillations occurred from the samples of the signals used to obtain energy and event coordinates.

The event locator circuits 930 in some implementations, form part of a data acquisition processing system 932 that processes the signals produced by the acquisition circuits 926. The data acquisition processing system 932 usually includes a general controller 934 that controls communications for example, by way of a backplane bus 936, and on the general communications network 918. The event locator circuits 930 assemble the information regarding each valid event into a set of numbers that indicate precisely when the event took place (timing information), the position in which the event was detected and the energy deposited by the photon (energy information). This event data packet is conveyed to a coincidence detector 938 that is also part of the data acquisition processing system 932. Accordingly, with respect to the method 700 described above, process block 702 can be executed by the acquisition circuits 926 and the event locator circuits 930 assembling detection signals produced by detector units 922 into event data packets that indicate when each event took place, the position in which each event was detected, and the energy deposited by each event.

Figure 2B:
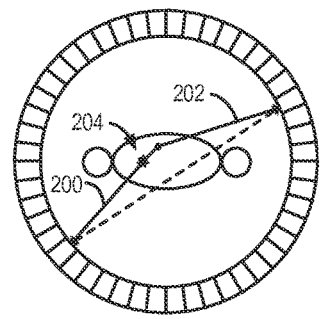
Figure 2C:
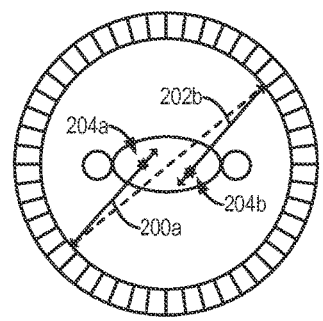

Referring back to the PET system 900, the coincidence detector 938 accepts the event data packets from the event locator circuit 930 and determines if any two of them are in coincidence. Coincidence is determined by a number of factors. First, the energy associated with each event data packet must fall within a predefined energy acceptance window, such as from 511 keV−$\Delta E_1$ to 511 keV+$\Delta E_2$ (where $\Delta E_1$ and $\Delta E_2$ are chosen as a function of the energy resolution of the block detectors). Second, the time markers in each event data packet must be within a predetermined time window, for example, 5 nanoseconds or even down to picoseconds. The system 900 includes a timing resolution sufficient to identify events within this timing window (such as a nanosecond timing resolution or a picoseconds timing resolution). Third, the locations indicated by the two event data packets must lie on a straight line that passes through the field of view in the scanner bore 914. Coincidences that fall under these factors can be considered prompt coincidences, including true coincidences (as shown in FIG. 2A), in-body scatter coincidence (as shown in FIG. 2B), and random coincidences (as shown in FIG. 2C). Coincident event pairs are located and recorded as a coincidence data packet by the coincidence detector 938. This coincidence data packet, which constitutes traditional PET data, will be referred to as dataset 1.

The coincidence detector 938 can also determine if any three or more events are in coincidence (that is, as an MD event or, in other words, an IDS event, a random MD event, or a positron-gamma MD event, among others) according to a separate set of factors. These multiple coincidence events can then be located and recorded as another coincidence data packet, which will be referred to as dataset 2. Traditionally, such data that cannot be paired, that is, in relation to double coincidences, is discarded from consideration by the coincidence detector 938.

Dataset 1, dataset 2, and other acquired data (such as non-coincidence data and/or other data corresponding to photon events with energy deviating from the standard 511 keV of an electron-positron annihilation event) are provided to a sorter 940. The function of the sorter in many traditional PET imaging systems is to receive the coincidence data packets and generate memory addresses from the coincidence data packets for the efficient storage of the coincidence data. In that context, the set of all projection rays, or lines of response, that point in the same direction (θ) and pass through the scanner's field of view (FOV) is a complete projection, or "view". The distance (R) between a particular line of response and the center of the FOV locates that line of response within the FOV. The sorter 940 counts all of the events that occur on a given line of response (R, θ) during the scan by sorting out the coincidence data packets that indicate an event at the two detectors lying on this line of response.

Because MD coincidence events involve more than two detectors, such events may be counted on one or more given lines of response (that is, a subset of lines of response) based on a specific sorting or recovering method. Once all events are counted, the coincidence counts are organized, for example, as a set of two-dimensional arrays, one for each axial image plane, and each having as one of its dimensions the projection angle θ and the other dimension the distance R. This θ by R map of the measured events is called a LOR histogram or, more commonly, a sinogram array. Typically, it is these sinograms that are processed to reconstruct images that indicate the number of events that took place at each image pixel location during the scan. The sorter 940 counts all events occurring along each line of response (R, θ) and organizes them into an image data array. As described above, in accordance with the present invention, MD coincidence events can be sorted separately from double coincidence events. Normalization correction can then be separately applied to both sets of sorted events and the normalized data can be organized as one or more image dataset arrays. Alternatively, normalization can be applied inside of an iterative reconstruction method and, as a result, separate sets of double coincidence event data and MD coincidence event data can be organized by the sorter 940 into image dataset arrays without normalization correction applied.

The sorter 940 provides the image dataset arrays to an image processing/reconstruction system 942, for example, by way of a communications link 944 to be stored in an image array 946. The image array 946 holds the dataset array for access by an image processor 948 that reconstructs one or more images corresponding to the dataset array. In some applications, normalization correction may be applied at the image processing/reconstruction system 942 rather than at the sorter 940, or at a separate, intermediate system. Accordingly, with respect to the method 700 of FIG. 7, process blocks 704, 706, and 708 can be executed by the coincidence detector 938 and the sorter 940, process blocks 710, 712, and 714 can be executed by the sorter 940, the processing/reconstruction system 942, or a separate, intermediate system, and process block 716 can be executed by the processing/reconstruction system 942 (in particular, the image processor 948).

The methods described herein provide an improvement in sensitivity that can be adopted in existing preclinical and clinical PET scanners, such as that described above with respect to FIG. 9, without requiring any hardware modifications. For example, traditionally, performance parameters are very similar among commercially available PET scanners with similar hardware, and there is an almost linear trend between the quantity of detector material used in the scanner, its sensitivity, and its price. However, the present invention can provide a competitive advantage to current commercially available scanners, since sensitivity can be increased using data that is readily available without requiring additional materials and, thus, additional material costs. Depending on the scanner, patient size, and types of MD events used for image reconstruction, the method of the present invention can provide more than a 20% increase in sensitivity compared to traditional PET images. The present invention further provides methods to effectively use this readily available data to increase the image quality.

Though described with reference to the PET system 900, these methods are not limited to the use of scintillator-type block detectors, but may be executed on other systems with radiation detectors. For example, these processes may also be executed in PET systems using high-granularity detectors. In addition, the present invention may be used in other PET applications that utilize n-coincidence photons (that is, more than two photons detected simultaneously). In other words, the methods of the present invention are not specific to the types of MD coincidences events defined in the text. As described above, because the sensitivity profiles for double- and n-coincidence events are different, it is clear that a separate normalization correction can improve any application that uses n-coincidence events.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. An emission tomography system for acquiring a series of medical images of a subject, the system comprising:
    a plurality of radiation detectors configured to be arranged around the subject to acquire photons emitted from the subject as a result of a radionuclide administered to the subject and communicate signals corresponding to acquired photons;
    a data processing system configured to:
    receive the signals from the plurality of detectors,
    determine, from at least the signals from the plurality of detectors, coincidence events including photon coincidence events involving two photons and photon coincidence events involving at least three photons,
    map the photon coincidence events involving two photons to projected lines of response,
    map the photon coincidence events involving at least three photons to the projected lines of response,
    apply a first normalization correction to the mapped coincidence events involving two photons based on a first normalization using two-photon events, and
    apply a second normalization correction to the mapped photon coincidence events involving at least three photons based on a second normalization using coincidence events involving at least three photons; and
    a reconstruction system configured to:
    receive from the data processing system an array of normalized photon coincidence events involving two photons,
    receive from the data processing system an array of normalized photon coincidence events involving at least three photons, and
    reconstruct therefrom a series of medical images of the subject.

2. The system of claim 1 wherein the data processing system is further configured to identify timing information and energy information of the acquired photons, wherein the timing information is identified with sufficient resolution to determine the photon coincidence events involving two photons and the photon coincidence events involving at least three photons.

3. The system of claim 2 wherein the timing resolution is at least one of nanosecond and picosecond resolution.

4. The system of claim 2 wherein the photon coincidence events involving at least three photons are mapped to the projected lines of response based on the timing information and the energy information.

5. The system of claim 1 wherein the reconstruction system is further configured to map photon coincidence events involving at least three photons based on the mapped photon coincidence events involving two photons.

6. The system of claim 1 wherein the photon coincidence events involving at least three photons are determined by a first set of factors and the photon coincidence events involving two photons are determined by a second set of factors, different from the first set of factors.

7. The system of claim 1 wherein data for the first normalization using two-photon events and data for the second normalization using photon coincidence events involving at least three photons are obtained from a single acquisition.

* * * * *

UNITED STATES PATENT AND TRADEMARK OFFICE
CERTIFICATE OF CORRECTION

PATENT NO. : 10,502,846 B2  
APPLICATION NO. : 14/897105  
DATED : December 10, 2019  
INVENTOR(S) : Eduardo M. Lage et al.

Page 1 of 2

It is certified that error appears in the above-identified patent and that said Letters Patent is hereby corrected as shown below:

In the Specification

Column 15, Lines 5-8, Eq. 1, " $x_j^{(n+1)} = x_j^{(n)} \cdot \left[ \sum_i \alpha_{ij} \cdot \left( \dfrac{\dfrac{g_i^D + g_i^{MD}}{N_i^D}}{\lambda_i} \right) \right] / \sum_i \alpha_{ij}$ " should be -- $x_j^{(n+1)} = x_j^{(n)} \cdot \left[ \sum_i \alpha_{ij} \cdot \left( \dfrac{\dfrac{g_i^D + g_i^{MD}}{N_i^D}}{\lambda_i} \right) \right] / \sum_i \alpha_{ij}$ --.

Column 15, Lines 18-22, Eq. 2, " $x_j^{(n+1)} = x_j^{(n)} \cdot \left[ \sum_i \alpha_{ij} \cdot \left( \dfrac{\dfrac{g_i^D}{N_i^D} + \dfrac{g_i^{MD}}{N_i^{MD}}}{\lambda_i} \right) \right] / \sum_i \alpha_{ij}$ "

Signed and Sealed this  
Twenty-fifth Day of February, 2020

Andrei Iancu  
*Director of the United States Patent and Trademark Office*

CERTIFICATE OF CORRECTION (continued)
U.S. Pat. No. 10,502,846 B2 should be -- $$x_j^{(n+1)} = x_j^{(n)} \cdot \left[ \sum_i \alpha_{ij} \cdot \left( \frac{\frac{g_i^D}{N_i^D} + \frac{g_i^{MD}}{N_i^{MD}}}{\lambda_i} \right) \right] / \sum_i \alpha_{ij}$$ --.

Column 15, Lines 35-38, Eq. 3,

" $$x_j^{(n+1)} = x_j^{(n)} \cdot \left[ \sum_i \alpha_{ij} \cdot \left( \frac{g_i^D + g_i^{MD}}{\lambda_i} \right) \right] / \sum_i \alpha_{ij} \cdot (N_i^D + N_i^{MD})$$ " should be -- $$x_j^{(n+1)} = x_j^{(n)} \cdot \left[ \sum_i \alpha_{ij} \cdot \left( \frac{g_i^D + g_i^{MD}}{\lambda_i} \right) \right] / \sum_i \alpha_{ij} \cdot (N_i^D + N_i^{MD})$$ --.